United States Patent [19]
Simon et al.

[11] Patent Number: 5,724,994
[45] Date of Patent: Mar. 10, 1998

[54] FLUIDLY EXPANDABLE URETHRAL PLUG ASSEMBLY WHICH RECEIVES FLUID FROM AN EXTERNAL SOURCE AND METHOD FOR CONTROLLING URINARY INCONTINENCE

[75] Inventors: John G. Simon, Boston; Carl J. Wisnosky, Spencer; Paul D. McLaughlin, Scituate; Sharad Joshi, Watertown, all of Mass.; Leo C. Felice, Pascoage, R.I.; Christopher C. Coulter, Newton Upper Falls, Mass.

[73] Assignee: UroMed Corporation, Needham, Mass.

[21] Appl. No.: 432,276

[22] Filed: May 1, 1995

Related U.S. Application Data

[63] Continuation-in-part of Ser. No. 124,264, Sep. 20, 1993, and Ser. No. 103,812, Aug. 6, 1993, which is a continuation of Ser. No. 746,364, Aug. 16, 1991, abandoned, which is a continuation-in-part of Ser. No. 636,285, Dec. 31, 1990, Pat. No. 5,090,424.

[51] Int. Cl.$^6$ .................................................. A61F 5/48
[52] U.S. Cl. ........................ 128/885; 128/DIG. 25; 600/38
[58] Field of Search ................ 128/885, DIG. 25; 600/38–40

[56] References Cited

U.S. PATENT DOCUMENTS

| | | | |
|---|---|---|---|
| 2,324,520 | 7/1943 | Lamson | 128/283 |
| 2,494,393 | 1/1950 | Lamson | 128/1 |
| 2,638,093 | 5/1953 | Kulick | 128/133 |
| 3,503,400 | 3/1970 | Osthagen et al. | 128/349 |
| 3,538,917 | 11/1970 | Selker | 128/326 |
| 3,646,929 | 3/1972 | Bonnar | 128/1 |
| 3,726,277 | 4/1973 | Hirschman | |
| 3,789,828 | 2/1974 | Schulte | 128/1 |
| 3,797,478 | 3/1974 | Walsh et al. | 128/1 R |

(List continued on next page.)

FOREIGN PATENT DOCUMENTS

| | | |
|---|---|---|
| 0328421 | 8/1989 | European Pat. Off. . |
| 2431888 | 1/1976 | Germany . |
| 8810106 | 12/1988 | WIPO .................. A61F 2/48 |
| 9004431 | 5/1990 | WIPO .................. A61M 29/00 |
| 9110466 | 7/1991 | WIPO .................. A61M 25/00 |
| 9219192 | 11/1992 | WIPO .................. A61F 5/48 |

OTHER PUBLICATIONS

Nielsen et al., "The Urethral Plug: A New Treatment Modality for Genuine Urinary Stress Incontinence in Women", Nov. 1990, pp. 1199 1202, Journal of Urology, vol. 144.

*Primary Examiner*—Michael A. Brown
*Attorney, Agent, or Firm*—Lorusso & Loud

[57] ABSTRACT

A novel urethral plug comprising a cooperating shaft and balloon, lying in coaxial engagement. The balloon possesses a contracted shape for insertion and removal through the opening of the urethra, and a larger, expanded shape for blocking the flow of urine in the urethra, bladder neck and bladder. After insertion, such an expanded shape is achieved by inflation of the balloon through the use of an external source such as a syringe which introduces fluid through an opening and into the shaft. The fluid acts upon a ball valve, thus pushing the ball past a valve seat, thereby permitting fluid to travel through the shaft and into the balloon. Fluid transmission continues until the balloon is expanded to such an extent as to block the flow of urine. The balloon retains the fluid therein, and the force of the fluid on the ball valve causes the ball to rest firmly against the valve seat. The balloon, when expanded thus functions to seal the plug to the urethra, bladder neck and bladder. Deflation of the plug for bladder evacuation, is easily accomplished by pulling a cord causing the removal of the ball from the valve seat towards the proximal end of the plug and out of the aperture, thus expelling the fluid contained within the balloon. Removal is then easily and comfortably accomplished by grasping a tab associated with said meatal plate, at which point the wearer can void. There is further provided a urethral plug assembly comprising a urethral plug with applicator and mirror for ease of insertion and inflation of the plug in a sterile manner.

52 Claims, 7 Drawing Sheets

U.S. PATENT DOCUMENTS

| | | | |
|---|---|---|---|
| 3,812,841 | 5/1974 | Isaacson | 128/DIG. 25 |
| 3,841,304 | 10/1974 | Jones | 128/DIG. 25 |
| 3,857,394 | 12/1974 | Alemany . | |
| 4,019,499 | 4/1977 | Fitzgerald | 128/1 |
| 4,224,934 | 9/1980 | Scott | 600/40 |
| 4,258,704 | 3/1981 | Hill | 128/1 R |
| 4,261,340 | 4/1981 | Baumel et al. . | |
| 4,428,365 | 1/1984 | Hakky | 128/1 |
| 4,457,299 | 7/1984 | Cornwell | 128/1 |
| 4,553,533 | 11/1985 | Leighton | 128/1 |
| 4,682,592 | 7/1987 | Thoregard | 128/303 |
| 4,686,985 | 8/1987 | Lottick | 128/344 |
| 4,795,510 | 1/1989 | Wittrock | 156/64 |
| 4,822,347 | 4/1989 | MacDougall . | |
| 4,846,784 | 7/1989 | Haber | 600/29 |
| 4,850,963 | 7/1989 | Sparks et al. | 600/29 |
| 4,938,759 | 7/1990 | Enscore et al. | 604/896 |
| 4,946,449 | 8/1990 | Davis, Jr. | 604/256 |
| 4,969,474 | 11/1990 | Schwarz | 128/885 |
| 4,981,465 | 1/1991 | Ballan et al. | 600/32 |
| 4,994,019 | 2/1991 | Fernandez et al. | 600/30 |
| 5,012,822 | 5/1991 | Schwarz | 128/885 |
| 5,019,032 | 5/1991 | Robertson | 600/29 |
| 5,024,658 | 6/1991 | Kozlov et al. | 604/96 |
| 5,074,855 | 12/1991 | Rosenbluth et al. . | |
| 5,090,424 | 2/1992 | Simon et al. | 128/885 |
| 5,097,848 | 3/1992 | Schwarz | 128/885 |
| 5,114,380 | 5/1992 | Larsen | 452/176 |
| 5,114,398 | 5/1992 | Trick et al. | 600/29 |
| 5,116,387 | 5/1992 | Berg | 623/66 |
| 5,131,906 | 7/1992 | Chen | 600/29 |
| 5,234,409 | 8/1993 | Goldberg et al. | 604/96 |
| 5,336,208 | 8/1994 | Rosenbluth et al. . | |
| 5,483,976 | 1/1996 | McLaughlin et al. . | |

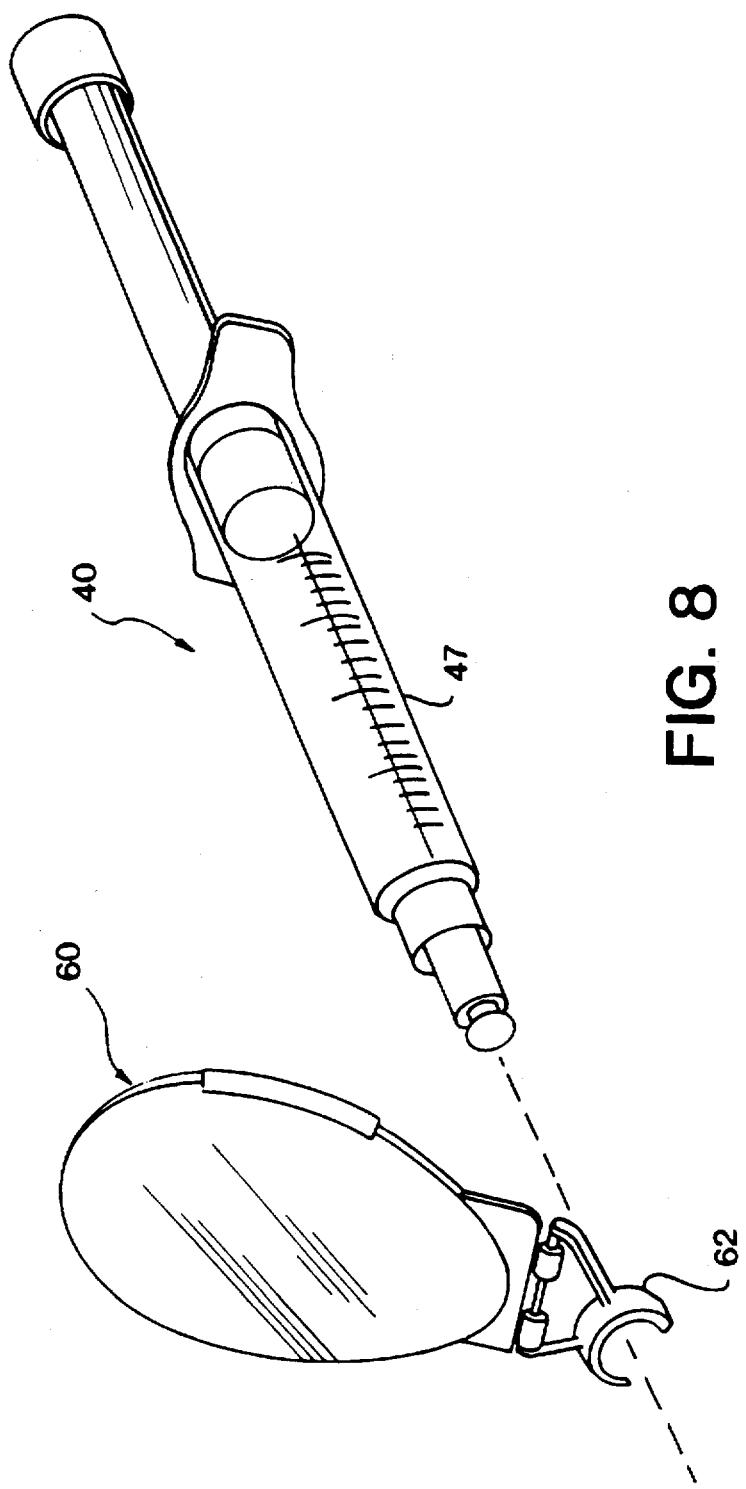

5,724,994

FLUIDLY EXPANDABLE URETHRAL PLUG ASSEMBLY WHICH RECEIVES FLUID FROM AN EXTERNAL SOURCE AND METHOD FOR CONTROLLING URINARY INCONTINENCE

CROSS REFERENCE TO RELATED APPLICATIONS

This application is a continuation-in-part of U.S. application Ser. No. 08/124,264 filed Sep. 20, 1993 and 08/103, 812 filed Aug. 6, 1993. U.S. application Ser. No. 08/103,812 is a continuation application of U.S. application Ser. No. 07/746,364 filed Aug. 16, 1991 (now abandoned), which is a continuation-in-part application of U.S. application Ser. No. 07/636,285 filed Dec. 31, 1990 (now U.S. Pat. No. 5,090,424), the teachings of the foregoing applications and patent being incorporated herein by reference.

DEFINITIONS

Various trademarks appear throughout the specification and claims to describe some of the chemical ingredients comprising the invention. They are identified as follows:

"KRATON G" is a trademark of Shell Oil Company and identifies the product styrene-ethylene/butylene styrene block co-polymer blend.

"C-FLEX" is a trademark of Consolidated Polymer Technologies, Inc. and identifies the product styrene-ethylene/butylene styrene block co-polymer blend.

"SARLINK" is a trademark of DSM Thermoplastic Elastomers Inc. and identifies a dynamically vulcanized thermoplastic elastomer product.

"DACRON" is a trademark of E.I. Du Pont De Nemours and Co. and identifies the product polyethylene terephthalate.

"SANTOPRENE" is a trademark of Monsanto Company and identifies thermoplastic elastomers, and more particularly, styrene block thermoplastic elastomers.

BACKGROUND OF THE INVENTION

1. Field of the Invention

The present invention relates to a novel occlusion device which is inserted into the urethra to control urinary incontinence.

2. Description of the Prior Art

Urinary stress incontinence is defined as the involuntary loss of urine when the pressure within the urethra exceeds the urethral closure pressure required for maintaining continence. While the problem of urinary incontinence occurs in men and women, it is an affliction especially common in women of child-bearing age and beyond.

There are in existence several methods used to address the problem of incontinence. Bladder neck suspension surgery, wherein the neck of the bladder is reduced by suspending the bladder, is a common way for surgeons to treat incontinence. However, there are numerous risks associated with such surgery, notwithstanding the expense. For some patients, bladder neck suspension surgery is not recommended for medical or other reasons. For example, in women who previously have undergone bladder neck surgery with unsuccessful results, an additional surgical procedure may be neither appropriate nor beneficial. Also, for those with mild incontinence surgery is not always a necessary solution.

Also in existence are a variety of devices for controlling urinary incontinence. Many of these devices require surgery for implantation, and of these surgically implanted devices, there are two distinct types: non-manipulable devices and manipulable devices. One such non-manipulable device, described in U.S. Pat. No. 4,019,499, is a capsule filled with a variable amount of fluid. The capsule is surgically implanted between supporting tissue and the urethra to exert an occluding force thereon. A similar, non-manipulable capsule implant is described in U.S. Pat. No. 3,789,828. However, this device has ties extending therefrom to aid in fiber ingrowth, thus providing mechanical stability to the capsule. One problem associated with this device is the risk of fluid leakage. In addition to problems with leakage, severe tissue damage may result from the unnatural method in which such devices regulate incontinence.

Other surgically implanted devices exist which are manipulable. These devices provide the wearer with the ability to selectively control the operation of the device via manually operable elements implanted in the tissue surrounding the urethra. U.S. Pat. No. 4,428,365, and U.S. Pat. No. 4,846,784 each disclose an indwelling device having an inflatable chamber with an attached tubing and an inflation bulb. The wearer may manually adjust the pressure exhibited by the inflatable member on the urethra, simply by squeezing the tissue encasing the bulb. These devices, however, often produce thickening and scarring of surrounding tissue, making their usefulness questionable. Additional adverse effects associated with surgically implanted indwelling devices, whether non-manipulable or manipulable in nature, are encrustation, irritation, infection, toxic reactions to materials, tissue necrosis and, occasionally, surgery to remove the device due to device failure or complications.

There are also known in the art, certain indwelling devices that do not require surgical implantation. These devices are inserted by a physician through the urethral orifice and allow the wearer to void either past or through the device. An example of such a device is disclosed in U.S. Pat. No. 4,850,963 in which a physician inserts a bolus of ferromagnetic material through the urethra and into the bladder. The bolus rests at the juncture of the bladder and urethra and is moved for bladder evacuation, by the relative positioning of a magnet across the body of the wearer. However, the bolus may become lodged in an area beyond the reaches of the magnetic force exhibited by the magnet, making the device inoperative. Another example of this type of indwelling device is the prestressed capsule disclosed in U.S. Pat. No. 4,457,299. The capsule is inserted by a physician within the lower interior of the urethra and is set at a prestressed pressure slightly above involuntary pressure. When the urine pressure exceeds the preset pressure of the capsule, the capsule deforms allowing urine to flow around the device. This device, however, has no feature to prevent migration of the device into the bladder. In U.S. Pat. No. 4,553,533 there is shown a prosthetic urethral sphincter valve which is placed in the urethra and anchored in the bladder. The patient increases his bladder pressure by means of a valsalva maneuver, and holds this pressure while the valve activates. Urine may then pass through the valve with the valve later returning to its closed position. This device is very complicated, expensive, difficult to manufacture and uncomfortable. Another physician-inserted device is disclosed in U.S. Pat. No. 3,797,478. This device has an expandable collar which is inflated after insertion, by an injection of fluid therein. When it is desired to remove the device, the inflated collar must be ruptured or serrated, thus expelling the fluid into the wearer's body. This makes it dangerous and difficult for the wearer to remove. Notwithstanding the cumbrous use of this device, there is a risk of infection associated with the long term indwelling time and with the release of injection fluid upon removal. Similarly, U.S. Pat. No. 3,841,304 discloses a plug which is inserted by a physician into the urethra and subsequently inflated to block the flow of urine. This device may be left in the body for extended periods. After insertion, the device merely requires repositioning in the urethra to permit bladder evacuation. Such a device leaves the wearer susceptible to infection, as bacteria may be introduced into the urethra during repositioning, or during indwelling time. Also, serious complications can occur upon removal, when a separate wire must be inserted therein. U.S. Pat. No. 5,114,398 discloses a flow-through plug which is left in the urethra for as long as desired. The device comprises a shaft having an inflatable balloon prior to its end. The shaft continues through the balloon, the shaft having a proximal opening and cooperating channel through which urine can pass. The excessive length of the shaft can cause irritation and complications such as catheter tip cystitis. The channel is closed by a valve until voiding is desired, at which point the wearer activates the valve causing it to open. Urine that has collected in the bladder then flows through the shaft, and out of the body. It is thus clear that the above devices, being indwelling, are often cumbersome to the wearer and often cause numerous complications such as encrustation, irritation and infection.

Also known in the art are devices capable of being inserted by the wearer into the urethra. Such devices are removed for voiding, and then reintroduced into the urethra upon completion of bladder evacuation. An example of such a device is the solid-type urethral plug, described by Nielsen, Kurt K. et al., in "The Urethral Plug: A New Treatment Modality for Genuine Urinary Stress Incontinence in Women" *J. Urology*, vol. 44, p. 1100 (1990). This device consists of one or two solid spheres located along a soft shaft, and a thin, soft plate located at the end of the shaft. One sphere is located upstream of the maximum urethral closing pressure point, corresponding to the location of the sphincter. In the two sphere embodiment, the second sphere is located with its midpoint at the bladder neck, and is used to assist in reducing urinary flow and pressure transmission to the urethra so that the sphincter can operate. When the patient wants to evacuate the bladder, the plug is removed, evacuation occurs, and a fresh plug is inserted. One problem associated with this device is that the patient must have three urethral closure pressure profiles performed as well as other examinations, before the device is made for the wearer. Additional problems associated with this device include placement difficulties, lack of sealing capabilities associated therewith, inadequate retention thereby allowing expelling and inadequate anchoring by the plate at the meatus. In addition to such problems is the discomfort associated with insertion due to the size profile and rigidity of the spheres, which maintain a constant diameter during insertion and removal. Another "remove-to-void" device is disclosed in U.S. Pat. No. 5,090,424, which comprises a conformable urethral plug. The body of the plug forms a cavity which is in fluid communication with another cavity via a check-valve. In that device the fluid used to inflate the plug is integral with the plug.

In view of the above discussion concerning problems and complications associated with prior art devices, it would be desirable to provide an easily manipulable, remove-to-void urethral plug having a fluidly expandable balloon inflated by a removably coupled external fluid source. Such a device would minimize the discomfort to the wearer while preventing unwanted involuntary flow of urine.

SUMMARY OF THE INVENTION

An object of the invention is to provide a device which controls the unwanted leakage of urine from the urethra.

Another object of the invention is to provide a removable device which arrests involuntary voiding of urine after insertion into the urethra, bladder neck or bladder followed by inflation.

Another object of the invention is to provide a removable urethral plug for preventing unwanted flow of urine which only allows voiding after deflation and removal of the plug by the wearer.

An additional object of the invention is to provide a urethral plug which is easily manipulated by the wearer.

A further object of the invention is to provide a urethral plug made of a material sufficiently stiff for ease of insertion yet sufficiently soft to conform to the urethra during typical body movements.

Another object of the invention is to stabilize the placement of a urethral plug at the urethral meatus, such that migration into the bladder will not occur.

Another object of the invention is to provide a urethral plug capable of anchoring in the urethra, bladder neck or bladder, such that expulsion of the plug from the body will not likely occur.

A further object of the invention is to improve the degree of comfort associated with insertion and removal of a urethral plug.

Yet another object of the invention is to provide a urethral plug assembly comprising an applicator for ease of insertion.

Another object of the invention is to provide a method for controlling incontinence.

Still another object of the invention is to provide a method of using a urethral plug while minimizing risk of contamination.

These and other objects of the invention are carried out by a novel urethral plug sufficiently rigid for ease of insertion into the urethra, yet sufficiently pliable to conform to the size and shape of the urethra during typical body movements. This is achieved by the structural design and material composition of the urethral plug.

The urethral plug comprises a cooperating shaft and balloon, lying in coaxial engagement. The balloon possesses a contracted shape for insertion and removal through the opening of the urethra, and a larger, expanded shape for blocking the flow of urine in the urethra, bladder neck and bladder. The expanded shape also serves to maintain the plug shaft's position in the urethra. Such an expanded shape is achieved by fluid inflation from an external source such as a specially adapted syringe or inflator. A fluid is introduced through an aperture and into a continuous channel in the shaft, whereby it acts upon a ball valve. The force of the fluid pushes the ball past a cooperating valve seat, thus permitting fluid to travel into the balloon causing it to expand. Once expanded and the external inflation source removed, the balloon retains the fluid therein, as the downward force of the fluid on the ball valve causes the ball to rest firmly against the valve seat. The unique design of the valve chamber in the shaft provides springs which mechanically help re-seat the ball valve when the external inflation source is removed.

Upon expansion, the balloon thus functions to seal the plug to the urethral, bladder neck and bladder wall. The plug further has a meatal plate for preventing migration into the bladder. Deflation of the plug for bladder evacuation, is easily accomplished by pulling a cord attached to the ball towards the proximal end of the plug causing the removal of the ball from the valve seat, thus allowing the fluid contained within the balloon to be expelled. Removal is then easily and comfortably accomplished by grasping a tab attached to the meatal plate, at which point the wearer can void.

In accordance with a further feature of the invention, there is provided an applicator specially adapted to be firmly and removably connected with the urethral plug to assist the wearer in easily locating the urethral opening and inserting the plug into the urethra. After insertion and inflation of the urethral plug, the applicator is easily detached therefrom. An applicator so adapted is advantageous in that it minimizes the risk of infection by eliminating human contact during preparation and insertion of the urethral plug into the body. For those requiring additional assistance in locating the urethral opening, a specially designed mirror is provided which adapts to the applicator.

In accordance with yet another feature of the invention, there is provided a method for controlling urinary incontinence in humans.

BRIEF DESCRIPTION OF THE DRAWINGS

FIG. 8 shows an exploded view of an applicator with mirror for use with the urethral plug of the invention.

DETAILED DESCRIPTION OF THE INVENTION

Figure 1:
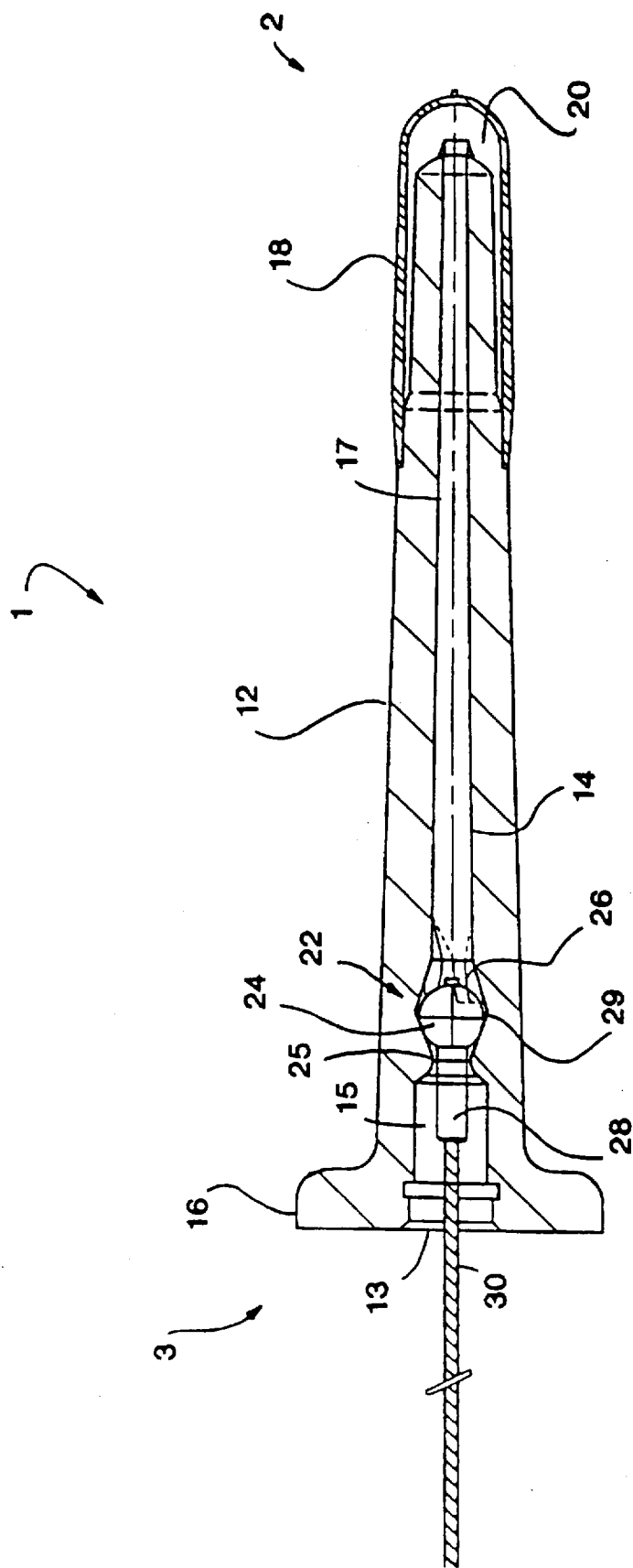
FIG. 1 shows the preferred embodiment of the urethral plug in its contracted configuration.

FIG. 1 shows the plug 1 of the instant invention in its pre-insertion state. The plug 1 of the present invention comprises a shaft portion 12 formed of a biocompatible deformable material. Suitable materials comprising the shaft portion 12 include but are not limited to thermoplastic elastomers and similar materials thereto, in particular, KRATON G, C-FLEX, polyurethane (or other similar thermoplastic urethanes), SARLINK, SANTOPRENE, poly-vinyl chloride, silicone, latex or other rubbers. For ease of insertion, the shaft portion 12 has a tapered tip on its distal end and a maximum diameter of less than 5 mm (15 French).

The shaft portion 12 has a central opening 13 and defines a central channel 14 through which fluid can flow, as is further explained. At the proximal end 3 of the shaft portion 12 is a meatal plate 16 further described in FIG. 4. Attached at the distal end 2 of the shaft portion 12, either by thermal bonding, laminating or other means, is a sealing membrane, or balloon 18, which in its pre-insertion configuration, is adapted to rest against the shaft portion 12. Suitable biocompatible materials comprising the balloon 18 include but are not limited to thermoplastic elastomers and similar materials thereto, in particular, KRATON G, C-FLEX, polyurethane (or other similar thermoplastic urethanes), SARLINK, SANTOPRENE, poly-vinyl chloride, silicone, latex or other rubbers. Channel 14 is in fluid communication with the interior 20 of the balloon 18. Positioned within the channel 14 is a chamber 29, which comprises a ball valve 22. The ball valve 22 includes ball 24 and a valve seat 25. The chamber 29 further provides springs 26, which increase the elastomeric tension of the chamber 29.

Suitable biocompatible materials for ball valve 22 include but are not limited to polypropylene, polyestertetraphalate, silk, DACRON, nylon and other similar thermoplastic materials. The most preferred material is nylon. Connected to the ball 24 is ball shaft 28 and cooperating cord 30. Materials suitable for cord 30 include but are not limited to polypropylene, polyester-tetraphalate, silk, DACRON, and other similar thermoplastic materials, with the most preferred material being nylon. In addition, a lubricant which aids in sealing and removing of the plug 1 can be applied internally to the valve seat 25. Suitable materials comprising the lubricant include but are not limited to propylene glycol (PPG), glycol, glycerin and silicone oil, with the most preferred material being polyethylene glycol (PEG). As to be discussed with respect to FIG. 2, a fluid source is adapted to be coupled with the plug 1 at the central opening 13 to transmit fluid past the ball valve 22 in the direction of the arrow to cause expansion of the balloon 18.

Figure 2:
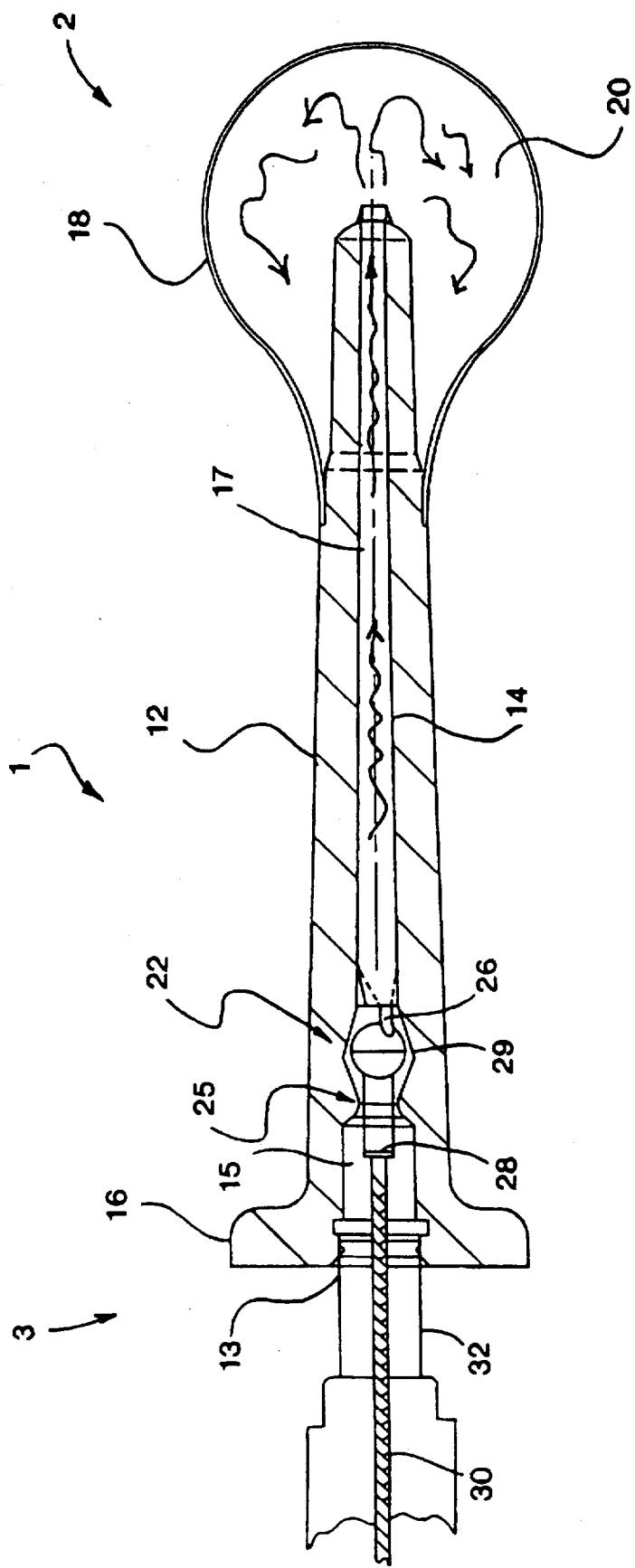
FIG. 2 shows the preferred embodiment of the urethral plug in its inflated configuration.

FIG. 2 shows the urethral plug 1 of the instant invention in its inflated and blocking state. To achieve this state, the wearer inserts the plug 1 into the urethra while it is in its pre-insertion configuration as shown in FIG. 1. The force required to insert the plug 1 is preferably less than 0.2 kg and, more preferably, less than 0.1 kg. Once inserted, fluid is then introduced into the channel 14 of shaft portion 12 by means of a conduit coupling 32 positioned at the central opening 13. The conduit coupling 32 can be the nozzle of a syringe, an inflator, a hose, or the like. In order for the fluid to enter the channel 14 of the shaft portion 12, the fluid must pass through a wide portion 15 of the channel 14 and displace the ball 24. When pressure is exerted through the wide portion 15 of the channel 14 in the direction shown by the arrows, the force of the fluid causes the ball 24 to move towards the distal end 2 of the plug 1. As the ball 24 moves toward distal end 2, it pushes against and temporarily deforms springs 26. Fluid is thereby allowed to pass into the narrower portion 17 of the channel 14 and ultimately into the balloon 18. The pressure required to inflate the plug 1 is preferably in the range of 1–20 psi, and more preferably 1–12 psi. The balloon 18 is inflated to a maximum diameter of less than 2.0 inches, preferably on the order of 0.4 inches to 1.0 inch, thereby sealing the device against the walls of the urethra, bladder neck or bladder to prevent incontinence.

At such time when sufficient fluid has been introduced to inflate the balloon 18, the back pressure of fluid in the balloon 18, together with the force exerted by springs 26, pushes the ball 24 towards the proximal end 3 of the plug 1 such that it again rests on the valve seat 25. The flow of fluid back through the ball valve 22 through which it entered is thereby prevented. At this point, the internal pressure within the balloon may reach a maximum of 15 psi, with a preferable range of about 6–13 psi. The balloon 18 in its inflated state serves to resist internal bladder pressure spikes of up to 3.0 psi (210 cm $H_2O$). Such bladder pressures would tend to expel the plug 1 unwarrantedly, for example, during coughing unless the balloon has been inflated.

Figure 3:
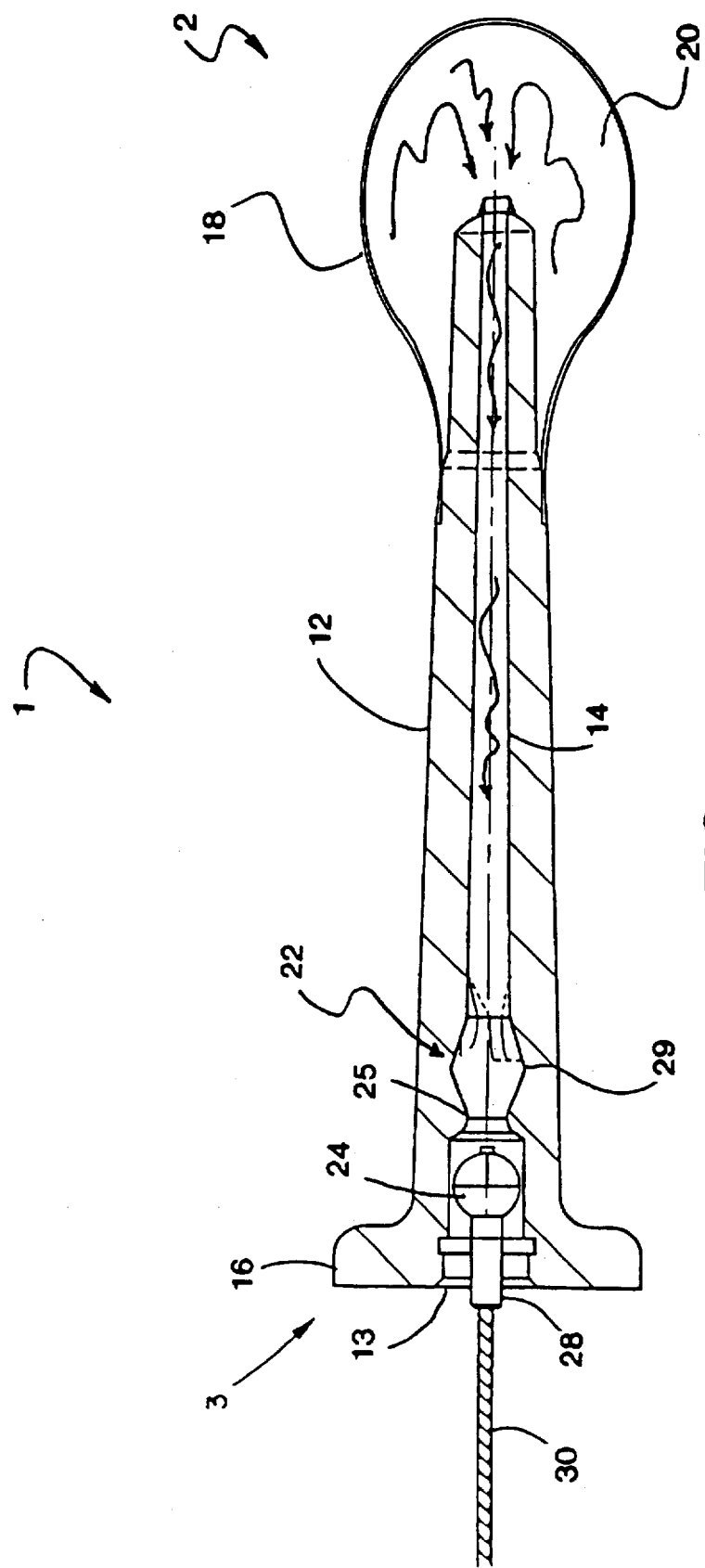
FIG. 3 shows the preferred embodiment of the urethral plug with the valve in an open position permitting deflation.

As shown in FIG. 3, when the wearer wishes to void, voiding is accomplished by grasping cord 30 and pulling it in a direction away from the proximal end 3 of the plug 1. This will exhibit a force on the ball 24 causing deformation of valve seat 25, thus allowing the ball 24 to move towards the proximal end 3 of the plug 1 and into the widened portion 15 of channel 14. The amount of force to be applied to the cord 30, and pull the ball 24 into the widened portion 15, is less than 1.5 lb., and preferably less than 0.8 lb for optimum comfort. Alternatively, the valve seat 25 can be deformed directly by pinching the plug 1 just above the meatal plate.

Either deflation means will allow fluid from the balloon 18 to be expelled through the channel 14, whereupon it exits the plug 1 through the central opening 13. Once the fluid in the balloon 18 has been expelled, the wearer can grasp the meatal plate 16 for removal of the plug. The force required to remove the plug 1 after deflation is preferably less than 0.1 kg and, more preferably, less than 0.05 kg to assure comfort of the wearer while removing the plug 1. Once removed and bladder evacuation accomplished, the wearer can insert a new plug. The used urethral plug 1 is disposed of through ordinary trash means.

To maintain sterility and minimize the risk of urinary tract infections, the urethral plug 1 of the invention has been designed to prevent re-use of the plug 1 after removal from the body. In an exemplary embodiment, this is accomplished when the ball 24 is disposed in the widened portion 15 of channel 14. In this way the ball valve 22 becomes inoperable so the urethral plug 1 cannot be re-used, i.e., cannot be re-inflated by the wearer. It should be recognized that it is within the scope of the present invention to use any means known in the art for controlling the flow of fluid into and out of the balloon 18, as well as means for rendering the valve inoperable to prevent re-use of the urethral plug 1.

Figure 4:
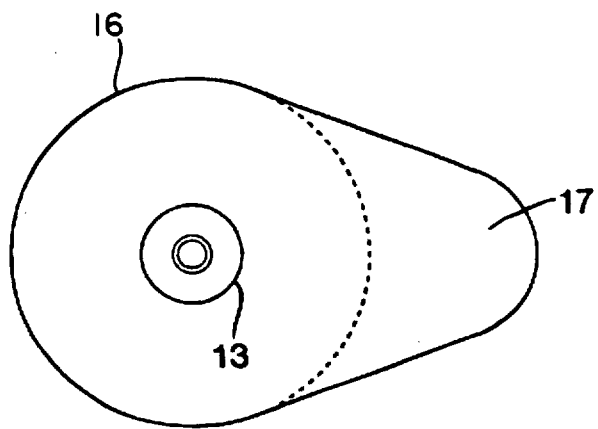
FIG. 4 shows a perspective view of the meatal plate of the urethral plug of the preferred embodiment.

FIG. 4 shows a perspective view of the meatal plate 16. The meatal plate 16 is adapted to anchor the urethral plug 1 at the meatus urinarius. To carry out this function of anchoring, the meatal plate 16 is of a thickness preferably in the range of about 1.0 mm to about 3.0 mm, with the most preferred thickness being 2.5 mm. This range of thickness of the meatal plate is sufficient to withstand bodily compression during wear. The meatal plate 16 is preferably greater than 8.0 mm in diameter, a diameter generally sufficient to prevent migration into the bladder. A portion of the meatal plate 16 is extended to form a flexible tab 17 which may be grasped by the wearer to remove the plug 1. The meatal tab 17 is of a preferred thickness of about 0.5 mm to about 2.0 mm for comfort and ease of removal.

The meatal plate 16 has an aperture therein which forms the central opening 13 to the shaft portion 12. The meatal plate 16 prevents the plug 1 from passing through the opening of the urethra ultimately leading into the bladder neck or bladder.

Figure 5:
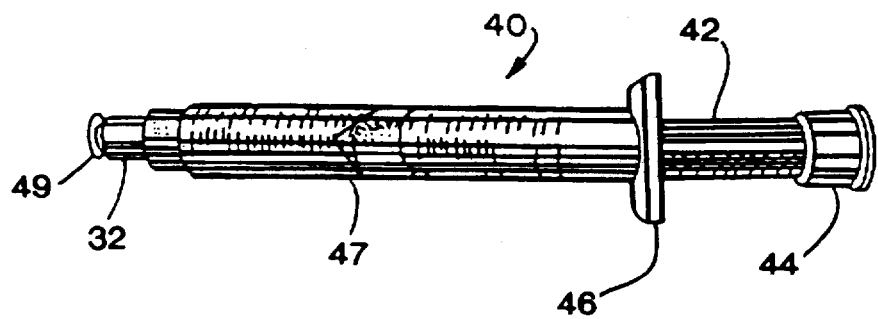
FIG. 5 shows an applicator for use with the urethral plug of the invention.
Figure 6:
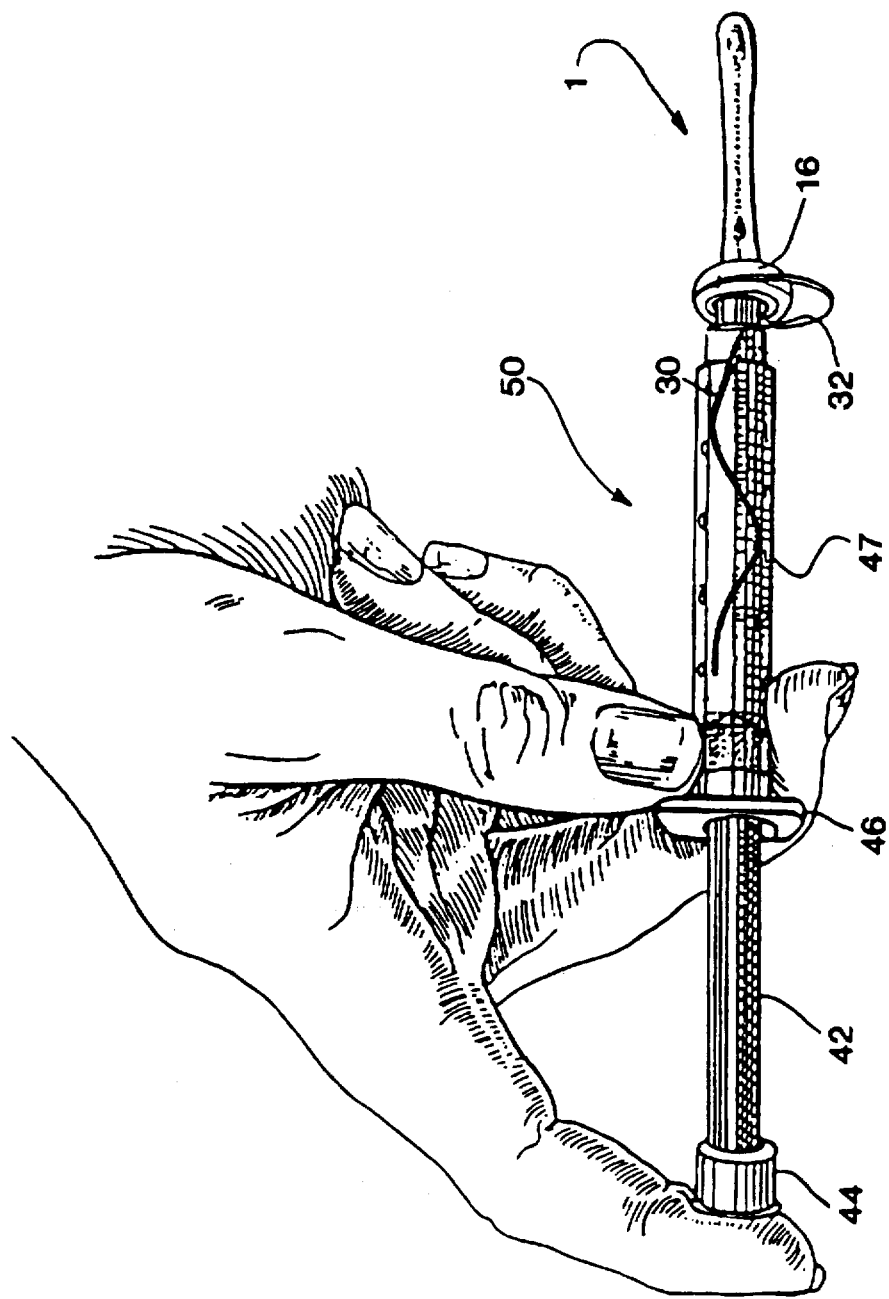
FIG. 6 shows a urethral plug assembly in a pre-insertion state.
Figure 7:
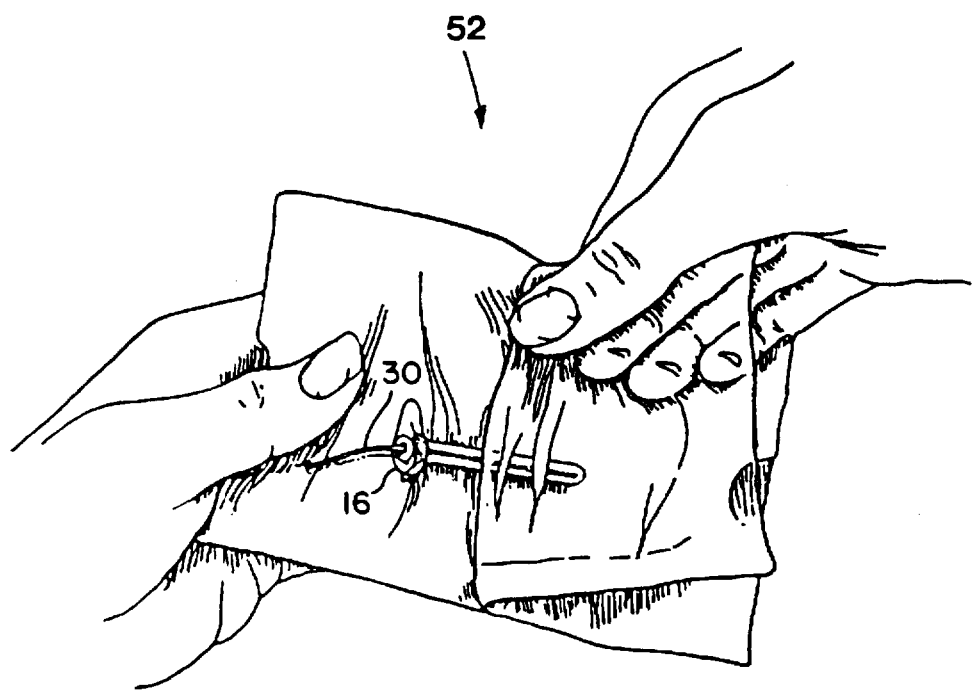
FIG. 7 shows how a user would open the sterile package of a urethral plug without touching the plug.

As shown in FIGS. 5 and 6, an applicator 40 is separately provided to assist the wearer in easily locating the urethral opening and inserting the urethral plug 1 into the urethra. A further advantage of the applicator 40 is to minimize the risk of infection by eliminating human contact during preparation of the urethral plug assembly 50, as shown in FIG. 6. This is accomplished by the sterile packaging of the plug 1 together with the practice of the following method. The user takes the applicator 40 from its sterile package and fully withdraws the plunger 42 to a position as shown in FIG. 6. FIG. 7 shows the wearer partially opening a package containing a sterile urethral plug 1 so as to expose the meatal plate 16 and chord 30, as shown. The partially opened package 52 containing the exposed plug 1 now serves as a protective sheath, thereby preventing human contact with the sterile plug 1 while attaching the applicator 40. Grasping the partially opened package 52, the user guides the cord 30 into the opening (not shown) in the conduit coupling 32 of the applicator 40 until the tip 49 of conduit coupling 32 forms a snap-fit with the central opening 13 of the meatal plate 16. Holding the urethral plug assembly 50 with one hand, the wearer positions the urethral plug assembly 50 at the urethral opening and inserts the plug 1 into the urethra until the meatal plate 16 contacts the opening. The wearer depresses the plunger 42 until the stop 44 abuts the applicator flange 46 of barrel 47. The balloon 18 of plug 1 is now fully inflated, as shown in FIG. 3. The applicator 40 is disengaged from the plug 1 by gently tilting in an upward direction.

The conduit coupling tip 49 and the meatal plate central opening 13 are removably connected by any of a number of means known in the art, including but not limited to snap-fit/de-fit type of connections and twisting and locking type of connections, that can establish a fluid pressure boundary, while retaining the ability to be easily removed without significantly disturbing the urethral plug 1 positioned and secured in the urethra. Preferably, the conduit coupling tip 49 and the meatal plate central opening 13 are interconnected by means of a snap-fit/de-fit type of connection, where the coupling/decoupling force is up to about 8 lbs, and preferably is a force of up to 6 .lbs, and most preferably, is a force of about 1 lb or less.

As a further aid in easily and accurately locating the urethral opening, a mirror 60 is provided, as shown in FIG. 8, which may be affixed to the barrel 47 of the applicator 40. One embodiment provides for the attachment of the mirror 60 with a clasp 62.

While the invention has been particularly shown and described with reference to the aforementioned embodiments, it will be understood by those skilled in the art that various changes in form and detail may be made therein without departing from the spirit and scope of the invention. Thus, any modification of the shape, configuration and composition of the elements comprising the invention is within the scope of the present invention. For example, the ball valve 22 described above may be located at various points along channel 14 of the plug 1.

We hereby claim:

1. A remove-to-void plug for use in the urethra to control urinary incontinence, said plug to be inserted into the urethral opening, comprising:

a plug forming body being closed to urine having a channel therein and having a proximal end and a distal end, a fluid-impermeable balloon affixed to the distal end of said plug forming body and fluidly coupled with said channel, said balloon having an outer surface free of protrusions, a valve positioned within said channel of said plug forming body, said valve having a chord affixed thereto, a fluid source external to said plug forming body, said fluid source being removably coupled to the proximal end of said plug forming body, said fluid source transmitting fluid through said channel, displacing said valve and inflating said balloon, said valve being reversely displaced after inflation to maintain said balloon in an inflated state.

2. The remove-to-void plug according to claim 1, said valve having a chord affixed thereto comprising a ball and a ball seat, respectively.

3. The remove-to-void plug according to claim 2, whereby said fluid transmitted by said fluid source displaces said ball from said ball seat.

4. The remove-to-void plug according to claim 2, whereby said valve maintains said balloon in an inflated state by a reverse pressure of said fluid which forces said ball against said ball seat.

5. The remove-to-void plug according to claim 2, wherein said chord is adapted to exert a force on said ball seat whereby said balloon deflates.

6. The remove-to-void plug according to claim 5, whereby the force to be applied to said cord is less than 1.5 lb.

7. The remove-to-void plug according to claim 6, whereby the force to be applied to said cord is less than 0.8 lb.

8. The remove-to-void plug according to claim 5 wherein said cord comprises a biocompatible material selected from the group consisting of polyestertetraphalate, polypropylene, silk, polyethylene terephthalate, nylon and other similar thermoplastic materials.

9. The remove-to-void plug according to claim 8 wherein the biocompatible material is nylon.

10. The remove-to-void plug according to claim 2, said valve further comprising a chamber having a plurality of springs protruding in said chamber, said plurality of springs being adapted to retain said ball in said chamber.

11. The remove-to-void plug according to claim 1, said valve comprising a biocompatible material selected from the group consisting of polyestertetraphalate, polypropylene, silk, polyethylene terephthalate, nylon and other similar thermoplastic materials.

12. The remove-to-void plug according to claim 11 wherein the biocompatible material is nylon.

13. The remove-to-void plug according to claim 1, said valve further including a lubricant, said lubricant selected from the group consisting of propylene glycol, glycol, glycerin, silicone oil and polyethylene glycol.

14. The remove-to-void plug according to claim 13 wherein said lubricant is polyethylene glycol.

15. The remove-to-void plug according to claim 1, wherein said fluid source comprises an applicator adapted to connect to the proximal end of said plug forming body.

16. The remove-to-void plug according to claim 15, wherein said applicator comprises a syringe or inflator.

17. The remove-to-void plug according to claim 1, said plug forming body further comprising a meatal plate adapted to anchor said plug at the urethral meatus.

18. The remove-to-void plug according to claim 17, said meatal plate having a thickness in the range of about 1–3 mm.

19. The remove-to-void plug according to claim 18, said meatal plate having a thickness of 2.5 mm.

20. The remove-to-void plug according to claim 17, said meatal plate comprising a tab extending therefrom, whereby said plug may be easily removed by a wearer when bladder evacuation is desired.

21. The remove-to-void plug according to claim 1, wherein said plug forming body comprises a thermoplastic elastomer.

22. The remove-to-void plug according to claim 1, wherein said plug forming body comprises a biocompatible material selected from the group consisting of polyurethane, silicone, latex, poly-vinyl chloride and styrene-ethylene/butylene styrene block co-polymer.

23. The remove-to-void plug according to claim 1, wherein said balloon comprises a thermoplastic elastomer.

24. The remove-to-void plug according to claim 1, wherein said balloon comprises a biocompatible material selected from the group consisting of polyurethane, silicone, latex, poly-vinyl chloride and styrene-ethylene/butylene styrene block co-polymer.

25. The remove-to-void plug according to claim 1, wherein said plug forming body comprises a shaft portion having a tapered tip on the distal end and a maximum diameter of less than 5 mm, said remove-to-void plug having a force of insertion of less than 0.2 kg and a force of expulsion of less than 0.1 kg with said balloon in a deflated state.

26. The remove-to-void plug according to claim 1, said balloon further having an inflation pressure in the range of about 1–20 psi and a diameter of inflation in the range of about 0.4–1 inch.

27. The remove-to-void plug according to claim 1, wherein said external fluid source further comprises a mirror.

28. The remove-to-void plug according to claim 1, wherein said plug forming body and said external fluid source are removably coupled with a snap-fit/de-fit type of connection.

29. The remove-to-void plug according to claim 1, wherein said plug forming body and said external fluid source are removably coupled so the connection is made and broken by applying a force of about 8 lbs or less.

30. The remove-to-void plug according to claim 29, wherein said plug forming body and said external fluid source are removably coupled so the connection is made and broken by applying a force of about 1 lb or less.

31. The remove-to-void plug according to claim 1, wherein said valve having a chord affixed thereto prevents re-use of the plug by the wearer when a force is exerted on said chord.

32. The remove-to-void plug according to claim 31, said meatal plate having a thickness in the range of about 1–3 mm.

33. The remove-to-void plug according to claim 32, said meatal plate having a thickness of 2.5 mm.

34. A remove-to-void plug for use in the urethra to control urinary incontinence, said plug to be inserted into the urethral opening, comprising:

a plug forming body closed to urine and having a distal end and a proximal end, said plug forming body defining a channel therein, a fluid-impermeable balloon affixed to the distal end of said plug forming body and fluidly coupled with said channel, said balloon having an outer surface free of protrusions, a valve positioned within said channel of said plug forming body, said valve comprising a ball and a ball seat, respectively, said ball further comprising a cord affixed thereto, a fluid source external to said plug forming body, said fluid source being removably coupled to the proximal end of said plug forming body, said fluid source transmitting fluid through said channel, displacing said ball from said ball seat and inflating said balloon, said ball reversely displaced against said ball seat after inflation to maintain said balloon in an inflated state, and wherein a force applied to said cord releases said ball from its position against said ball seat causing deflation of said balloon.

35. The remove-to-void plug according to claim 34, said valve further comprising a chamber having a plurality of springs protruding in said chamber, said plurality of springs being adapted to retain said ball in said chamber.

36. The remove-to-void plug according to claim 34, wherein said fluid source comprises a syringe adapted to connect to the proximal end of said plug forming body.

37. The remove-to-void plug according to claim 34, said plug forming body further comprising a meatal plate adapted to anchor said plug at the urethral meatus.

38. The remove-to-void plug according to claim 35, said meatal plate comprising a tab extending therefrom, whereby said plug may be easily removed by a wearer when bladder evacuation is desired.

39. A urethral plug assembly for prevention of urinary incontinence comprising:

a plug forming body being closed to urine and having a distal end and a proximal end, said plug forming body defining a single channel therein, a fluid-impermeable balloon affixed to the distal end of said plug forming body and fluidly coupled with said channel, said balloon having an outer surface free of protrusions, a valve positioned within said channel of said plug forming body, an applicator for positioning said plug in the urethra of a wearer, said applicator comprising a barrel having a coupling conduit for retaining said plug, and a plunger disposed in said barrel, said plunger adapted to push a fluid through said barrel and into said channel, said applicator being removably coupled to the proximal end of said plug forming body, said applicator transmitting said fluid through said channel and displacing said valve to inflate said balloon, said valve being reversely displaced after inflation to maintain said balloon in an inflated state.

40. The urethral plug assembly according to claim 39, said plug forming body further comprising a meatal plate adapted to anchor said plug at the urethral meatus.

41. The remove-to-void plug according to claim 40, said meatal plate having a thickness in the range of about 1–3 mm.

42. The remove-to-void plug according to claim 41, said meatal plate having a thickness of 2.5 mm.

43. The urethral plug assembly according to claim 40, said meatal plate comprising a tab extending therefrom, whereby said plug may be easily removed by a wearer when bladder evacuation is desired.

44. The urethral plug assembly according to claim 39, wherein said applicator further comprises a mirror.

45. A method for controlling urinary incontinence comprising the following steps:

a) providing a urethral plug being closed to urine comprising: a plug forming body having a channel therein and having a balloon affixed to the periphery thereof, said balloon being in fluid communication with said channel, b) inserting said urethral plug into the urethra via the urethral opening, c) transmitting fluid from an external fluid source through said channel causing inflation of said balloon, d) blocking the flow of urine with said balloon in its inflated state, e) pulling on a member integral with said urethral plug to deflate said balloon when the wearer wishes to void, f) removing said plug to void, g) repeating steps a)–f) with a new plug.

46. The method for controlling urinary incontinence according to claim 45 wherein said providing step further includes providing a mirror.

47. A method for controlling urinary incontinence comprising the following steps:

a) providing a urethral plug comprising; a plug forming body having a channel therein, an opening in the proximal end of said plug forming body, a balloon affixed to a distal end of said plug forming body, said channel fluidly connecting said opening with said balloon, and a valve positioned within said channel having an integral removal member connected thereto, b) placing an external fluid source in fluid communication with said opening, c) inserting said urethral plug into the urethra via the urethral opening, d) transmitting fluid from said fluid source through said channel causing displacement of said valve to allow fluid to pass therethrough, e) fluidly inflating said balloon, f) withdrawing said external fluid source from communication with said opening, g) blocking the flow of urine with said plug until voiding of the bladder is desired, h) pulling on said integral removal member causing said valve to open and said balloon to deflate, i) removing said plug, j) voiding the bladder, k) repeating steps a)–j) with a new plug.

48. The method for controlling urinary incontinence according to claim 47, wherein said providing step further includes providing a mirror removably affixed to said external fluid source.

49. The method for controlling urinary incontinence according to claim 47, wherein said steps of placing and withdrawing further includes a force of about 8 lbs or less to place and withdraw said external fluid source.

50. The method for controlling urinary incontinence according to claim 49, wherein said steps of placing and withdrawing further includes a force of about 1 lb or less to place and withdraw said external fluid source.

51. A method for controlling urinary incontinence comprising the following steps:

a) providing a urethral plug assembly comprising;

a plug forming body having an opening in the proximal end of said plug forming body, a balloon affixed to the distal end of said plug forming body, said channel fluidly connecting said opening with said balloon, said balloon being in fluid communication with said channel, an applicator for retaining said plug without human contact, said applicator adapted to push a fluid into said channel, said applicator being removably coupled to the proximal end of said plug forming body, and a mirror for attaching to said applicator;

b) attaching said mirror to said applicator;

c) positioning said urethral plug assembly at the urethral opening, d) inserting said urethral plug into the urethra via the urethral opening, e) manipulating the applicator whereby said fluid is transmitted from said applicator into said channel of said plug, causing inflation of said balloon, f) removing said applicator from said opening in the proximal end of said plug forming body, g) blocking the flow of urine with said balloon in its inflated state, h) pulling on a member integral with said urethral plug to deflate said balloon when the wearer wishes to void, i) removing said plug to void.

52. The method according to claim 51, further comprising the step of repeating steps a)–i) with a new plug.

* * * * *